United States Patent [19]

Schoendorfer

[11] 4,405,079

[45] Sep. 20, 1983

[54] CENTRIFUGAL DISPLACER PUMP

[75] Inventor: Donald W. Schoendorfer, Lexington, Mass.

[73] Assignee: Haemonetics Corporation, Braintree, Mass.

[21] Appl. No.: 205,144

[22] Filed: Nov. 10, 1980

[51] Int. Cl.³ .................. B04B 9/12; B04B 11/02
[52] U.S. Cl. ........................... 494/1; 494/10; 494/27; 494/44
[58] Field of Search ............... 233/23 A, 26, 23 R, 233/27, 1 A, 1 C, 1 R, 14 A, 14 R, 16, 19 R, 19 A, 20 R, 24, 16; 366/187; 137/56, 53; 251/7, 4; 128/272, 214 R; 222/47, 48, 41

[56] References Cited

U.S. PATENT DOCUMENTS

| | | | |
|---|---|---|---|
| 2,660,395 | 11/1953 | Mair et al. | 251/7 |
| 2,993,235 | 7/1961 | Brown et al. | 366/187 |
| 3,096,283 | 7/1963 | Hein | 233/20 |
| 3,420,410 | 1/1969 | Marder | 222/48 |
| 3,559,880 | 2/1971 | Naito et al. | 233/26 |
| 3,679,128 | 7/1972 | Unger et al. | 233/20 |
| 3,858,796 | 1/1975 | Unger et al. | 233/27 |
| 3,864,089 | 2/1975 | Tiffany et al. | 233/26 |
| 3,987,961 | 10/1976 | Sinn et al. | 233/20 R |
| 4,285,464 | 8/1981 | Latham, Jr. | 233/26 |

Primary Examiner—Philip R. Coe
Assistant Examiner—Timothy F. Simone

Attorney, Agent, or Firm—Hamilton, Brook, Smith and Reynolds

[57] ABSTRACT

Apparatus is disclosed for centrifugally separating blood into one or more components, such as a plasma-rich component, and a plasma-poor component. This apparatus employs a centrifuge intended to be used immediately adjacent to a blood donor. A flexible displacement container having a displacer fluid operated diaphragm is positioned within a blood processing chamber of the centrifuge rotor. The blood processing chamber comprises a pair of contoured support shoes which structurally supports the displacement container and a flexible blood processing container. Separated first blood component is expressed from the flexible processing blood container by movement of the diaphragm and is collected in a receiver container as the centrifuge rotor spins.

A reservoir for displacer fluid is mounted closer to the axis of rotation of the centrifuge than the flexible displacement container and in fluid communication therewith. The centrifugal force created by the spinning rotor creates a pressure differential between the reservoir and displacement container sufficient to pump the displacer fluid into said pouch, thus moving the diaphragm and expressing blood components from the blood processing bag.

3 Claims, 5 Drawing Figures

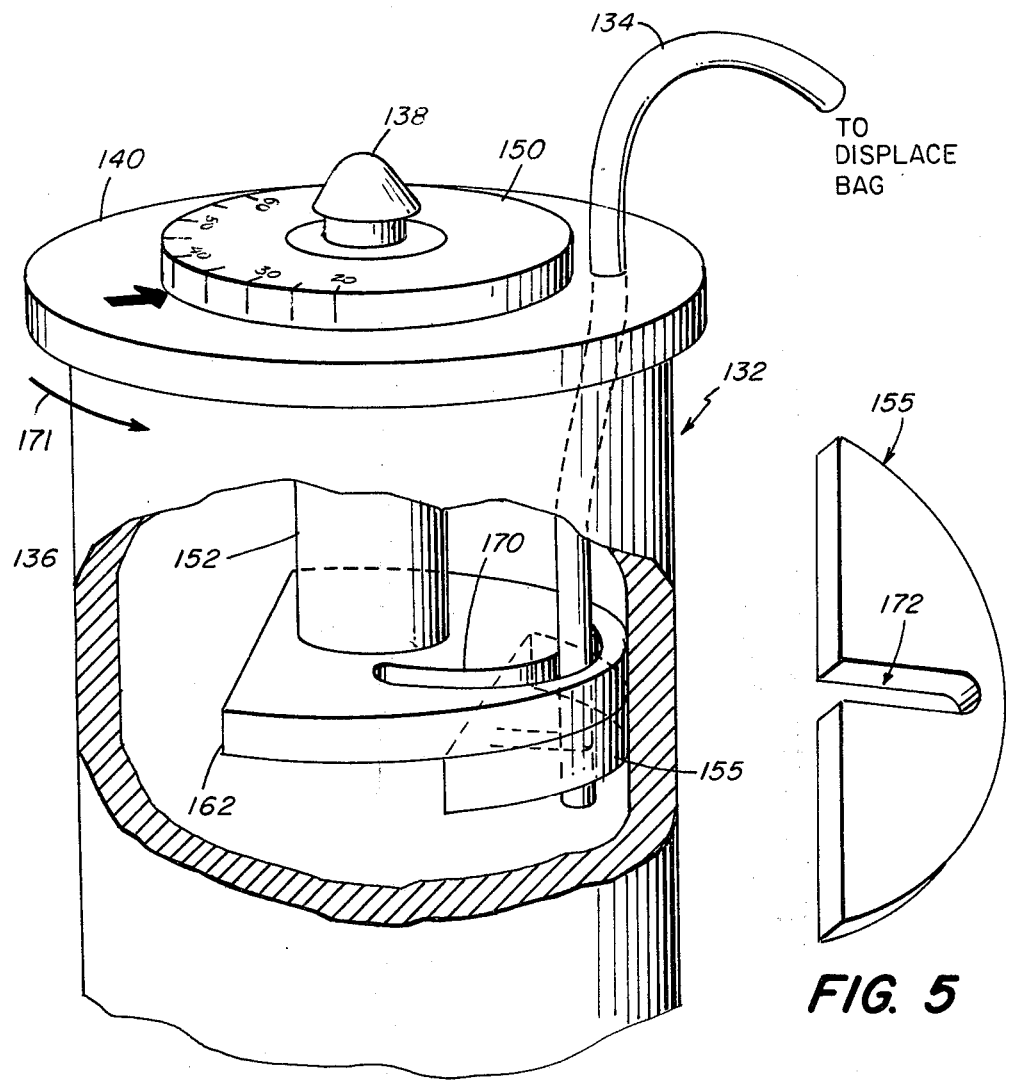

CENTRIFUGAL DISPLACER PUMP

DESCRIPTION

1. Technical Field

This invention is in the field of fluid processing and more particularly relates to the separation of blood, including whole blood, into two or more components.

2. Background Art

U.S. patent application Ser. No. 005,126 to Allen Latham, Jr. filed Jan. 22, 1979 (now U.S. Pat. No. 4,285,464) describes a centrifuge (hereafter the Latham centrifuge) for separating one or more components of blood into precise fractions or cuts.

In the Latham centrifuge, a flexible, disposable blood processing container, specifically a plastic bag, is mounted within a centrifuge rotor in a contoured processing chamber consisting of a pair of support shoes. The contoured chamber is designed to support the blood processing bag in a position whereby separated blood components traverse a short distance in the process of separation. A flexible diaphragm in the form of a displacer fluid container, such as one wall of flexible elastomeric bag (called a displacer bag), is also positioned in the blood processing chamber of the rotor in a complementary relationship to the flexible disposable blood bag. The flexible diaphragm can be made to apply pressure to the disposable blood bag in response to the introduction of a displacement fluid, either while the centrifuge rotor is rotating, or when it is stationary. Introduction of displacer fluid against the flexible diaphragm will result in the expression of separated blood components from the blood processing bag into one or more component receiver containers.

Often, it is desirable that this be accomplished while the rotor is rotating. In the Latham centrifuge and other similar devices, in order to pump displacer fluid to the displacer bag, fluid stored in a reservoir located external to the rotor, is pumped into the displacer bag by an auxiliary piston pump which is also located external to the rotor, as shown in the above referenced U.S. Pat. No. 4,285,464. In order to expand the flexible diaphragm while the rotor is spinning, the displacer fluid must pass through a rotary seal to reach the rotating displacer bag. The auxiliary displacer pump, though a relatively simple mechanical device, is composed of relatively expensive components. The necessity of a rotary seal makes the rotor assembly a much more difficult assembly to manufacture and service. In addition, leakage of air into, and fluid out of, the rotary seal is a serious problem, as it prevents flow of displacer fluid into the displacer bag.

Accordingly, a need exists for a simple, low cost apparatus and method for supplying displacer fluid in a centrifuge fluid processing device which apparatus is easy to install and eliminates the need for rotary seals.

DISCLOSURE OF INVENTION

The invention comprises an apparatus and process for separating fluid components such as blood components in a centrifuge. A typical application is the separation of plasma or other blood components from donated whole blood. A pair of processing containers in the form of plastic bags, a first one containing whole blood to be processed and a second one arranged to accept displacer fluid are disposed in complementary contacting relatioship within the contours of a pair of support shoes.

The support shoes are placed in the centrifuge rotor in an upright position adjacent the cylindrical outer wall of the rotor. A third container, called the component receiver container, is disposed on said rotor in fluid communication, with said first container, by means of plastic tubing interconnecting each. A cylindrical reservoir containing displacer fluid is also mounted on said rotor at a location radially inward from the location of the second container. This reservoir is maintained in fluid communication with the second, or fluid displacement, container by means of flexible plastic tubing.

The density of the displacer fluid is selected to be greater then the density of the fluid to be processed. When the rotor is rotated, the centrifugal force creates a positive pressure difference between the fluid in the reservoir, which is located nearer the rotor axis of rotation, and the fluid in the second container, which is further removed from the rotor axis.

As will be shown in detail in connection with the drawings, this pressure difference is utilized, in accordance with the invention, to provide the necessary pressure to pump displacer fluid from the reservoir to expand the displacer bag and thereby express an appropriate volume of separated fluid component from the first mentioned blood processing container into the component receiver container. Since the fluid displacement reservoir is located on the rotor, no rotary seals are required for fluid communication. Further, since the centrifugal force creates the pumping pressure no auxiliary pump is required.

A switch means responsive to centrifugal force is also provided intermediate the first and third containers to control the flow of fluid therebetween. This switch is operated by centrifugal force and therefore no slip rings or rotary seals are required to activate it.

There is further provided a control means for controlling the amount of displacer fluid communicated from the reservoir to the displacer bag. This control means, in a preferred embodiment, takes the form of an arcuate disk having a spiral groove therein which is rotatably mounted in the reservoir adjacent a fixed guide member which has a complementary radially directed slot. The tubing connecting the reservoir of displacer fluid and the displacer bag is passed through the groove and slot. Thus, the position of the tubing may be moved radially in response to the rotation of the disk thereby determining the amount of displacer fluid which may be removed from the reservoir by the centrifugal pumping action.

BRIEF DESCRIPTION OF THE DRAWINGS

FIG. 4 is a perspective view of a plasma volume controller in accordance with the invention.

FIG. 5 is a perspective view of a tube guide 155 used in the plasma volume controller of FIG. 4.

BEST MODE FOR CARRYING OUT THE INVENTION

Inasmuch as a general description of the centrifuge blood separation process to which this invention relates is contained in the above referenced U.S. Pat. No. 4,285,464, it is not necessary to reiterate such details here, it being understood, however, that like terms shall have a like meaning and that the apparatus shown herein, although it is intended to be used in a similar application, is not hereby limited thereto.

Figure 1:
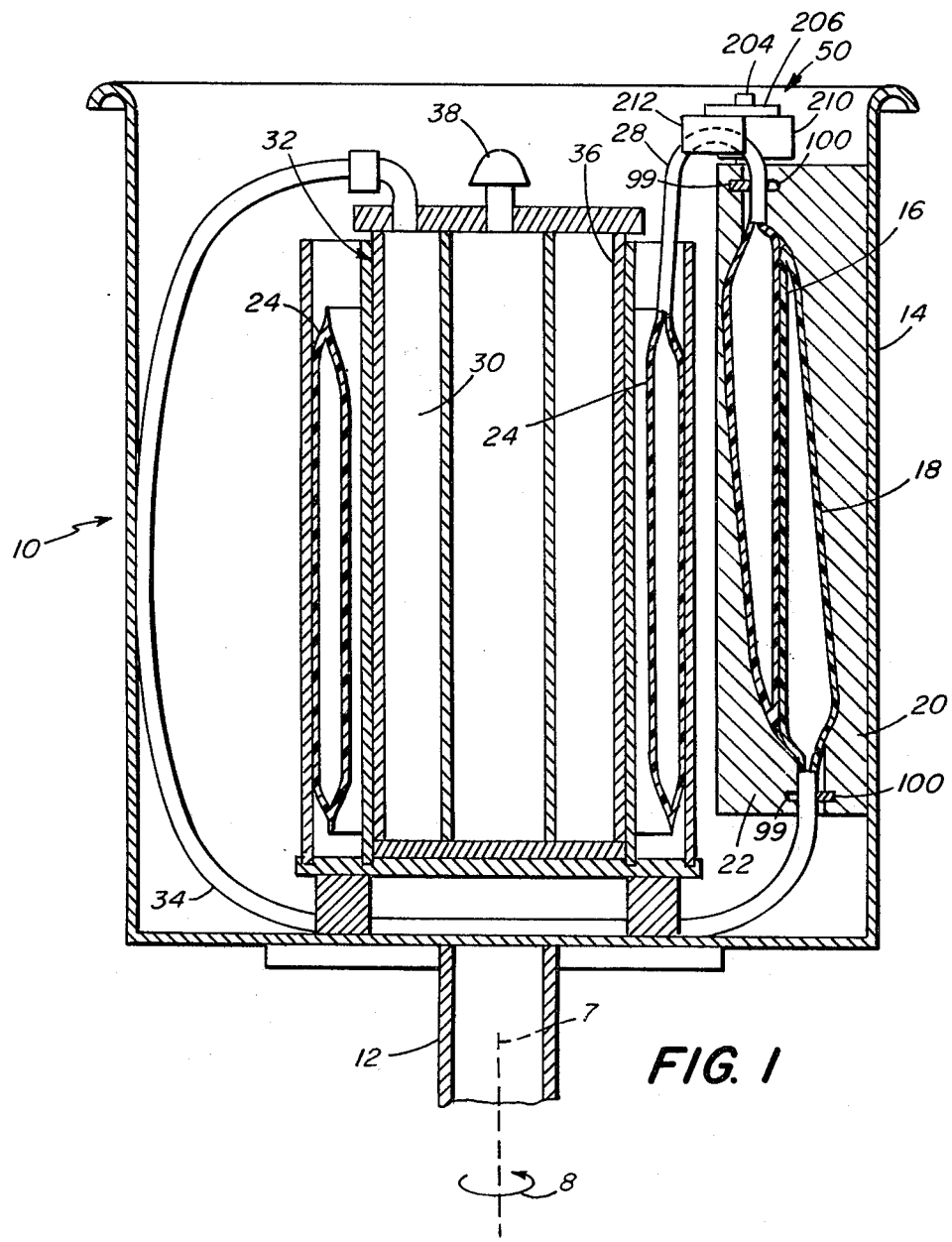
FIG. 1 is a cross-sectional view of a centrifuge in accordance with the invention.

Referring now to FIG. 1, there is shown a centrifuge 10 in accordance with the invention. The rotor 14 of the centrifuge is mounted on a shaft 12 which is rotably mounted on the centrifuge chassis (not shown) and is driven by a suitable motor (not shown) which may be either a variable speed motor or a two speed motor. Access to the interior of the rotor is provided at its top which is open. The rotor rotates about the axis of rotation 7 in the direction of arrow 8.

A blood processing bag 16 and a flexible displacer bag 18, are held in a complementary relationship in a contoured processing chamber formed between a pair of support shoes 20 and 22 mounted within rotor 14 against its inner wall.

Support shoes 20 and 22 can be formed from polymers such as foamed polyurethane. In some cases, it will be preferred to have transparent support shoes, in which case they can be formed from transparent polymers, such as polymethyl methacrylate. It is contemplated that many other materials could be used in forming these support shoes.

Since they do not have to be frequently removed, support shoe 20, reservoir 32 and tube 34 may be fixedly mounted on centrifuge rotor 14.

The displacer bag 18 may be attached to shoe 20 by suitable mechanical fasteners around its perimeter or by adhesives. Processing bag 16 is simply mounted on location pegs 99 on shoe 22. Shoe 22 is then closed onto shoe 20 so that the location pegs 99 extend into matching location peg holes 100 in the edge of shoe 20. In their closed position, shoes 20 and 22 form an enclosed contoured processing chamber containing blood processing bag 16 and fluid displacer bag 18, which are positioned so that their contacting planar panels assume a complementary relationship. Bag 16 is preferably supported by contoured shoe 22 so that bag 16 has an inner surface having a slightly greater slope at its upper portion than at its lower portion. This increased slope provides more efficient emptying during operation. Displacer bag 18 is contoured into a complementary shape by support shoe 20.

Flexible plastic tubing 28, at the top of bag 16, provides a fluid communicating connection between bag 16 and component receiver container 24. When blood processing bag 16 and displacer bag 18 are positioned in this complementary relationship within the contoured processing chamber, formed between support shoes 20 and 22, displacer bag 18 serves as a displacement chamber with its inner wall comprising a fluid-actuated diaphragm. As displacer fluid is introduced into displacer bag 18, it expands to force blood or blood components out of processing bag 16.

What has been described so far is substantially similar to the method and apparatus shown in the above referenced U.S. Pat. No. 4,285,464. This invention is generally concerned with the method and apparatus for providing displacer fluid to displacer bag 18.

In accordance with the invention, a source of displacer fluid 30, such as a solution of glycerin and water, or silicone oil, is provided in a reservoir 32 which is mounted on rotor 14 nearer the rotor axis of rotation than the blood processing chamber. In order to develop proper separation of separated blood components in the blood bag 16 and prevent distortions from forming in the diaphragm wall of the displacer bag, the displacer fluid should have a density greater than that of whole blood, that is, greater than a specific density of about 1.10.

A long length of flexible tubing 34 connects the displacer bag 18 to the displacer fluid reservoir 32. The reservoir 32 is slideably held within the rotor on reservoir frame 36 and may be readily lifted from the reservoir frame 36 for ease in cleaning, etc. An air vent 38 is provided on top of the reservoir to enable air to enter as displacer fluid 30 is centrifugally pumped into the displacer bag 18. The air vent also provides access as a filling port to replenish displacer fluid when required. A pinch clamp 50 is conveniently mounted on shoe 20. Tubing 28 passes through the pinch clamp 50 connecting the blood processing bag 16 to the component receiver container 24. Pinch clamp 50 is operable to control the flow of blood components to the receiver container and will be described in more detail in connection with FIGS. 2 and 3.

While only one component receiver bag 24 for plasma has been shown connected to a blood processing chamber, it is contemplated that additional receiver containers may be connected to the blood processing bag 16 to collect components when multiple blood components are expressed by the action of the displacer fluid bag in accordance with the invention. For example, after the plasma has been expressed from blood processing bag 16, a second cut consisting of platelets may be removed by suitably switching the flow in tubing 28 from the receiver container 24 to a second receiver container. Similarly, leukopheresis may be performed with a third receiver container.

It will be sufficient for the present description, however, to show the process in connection with plasma separation.

In operation, the system works as follows:

A centrifuge motor (not shown) is activated to cause centrifuge rotor 14 to rotate at a speed sufficient to separate withdrawn whole blood contained in processing bag 16 into a plasma-rich component and a plasma-poor component in a relatively short time (such as 5 minutes). A typical rotor speed, for example, might be about 2500 r.p.m.

As centrifuge rotor 14 rotates, plasma-poor component, which is heavier and consists primarily of red blood cells, white blood cells and platelets, moves towards the radially outer face of blood processing bag 16. This leaves lighter plasma-rich component near the radially inner face. The plasma-rich components can be expressed from processing bag 16 as centrifuge rotor 14 spins by introducing displacer fluid into displacer bag 18 thereby applying pressure to blood processing bag 16. This pressure causes plasma-rich component to be expressed through conduit 28 connected to the flexible blood processing bag 16. As will be explained below, pinch clamp 50 prevents the flow from bag 16 until sufficient time has elapsed to provide the desired separation of blood components within bag 16.

During the separation process, a positive pressure has been created in the blood bag 16 by the action of centrifugal force on the fluid 30 in reservoir 32, and in tube 34. This centrifugally created pressure is used to pump the displacer fluid out of reservoir 32 into displacer bag 18 which expands to express blood components from blood bag 16 through tubing 28 and into receiver container 24.

It should be emphasized that this is accomplished without the need for a separate mechanical pump, or rotary seals or complex fluid pathways.

Pinch clamp 50 is used to control the flow of blood components expressed from bag 16. It may consist of a fluid controlled clamp as shown in the above referenced U.S. patent application Ser. No. 005,126. However, this would again necessitate the use of an external pressure source and a rotary seal. Accordingly, a simpler mechanism is provided herein which is shown in greater detail in connection with FIGS. 2 and 3.

Figure 2:
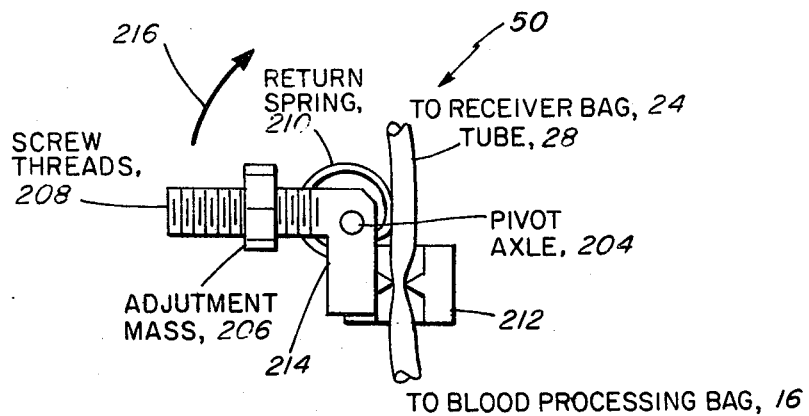
FIG. 2 is a side view of a centrifugal switch to be used in connection with the invention.

FIG. 2 depicts a centrifugal force switch type pinch clamp 50 mounted on a rotor (not shown) adapted to be rotated about an axis 202. The switch consists of a generally L-shaped member 214 capable of pivoting about pivot axle 204. One end of member 214 is provided with screw threads 208 and an adjustment mass 206 in the form of a nut is threaded thereon. A coil spring 210 is mounted in relation to member 214 so as to exert a force in the counterclockwise direction about pivot axle 204. At the remaining end of member 214 a projection extends into an opening between member 214 and a fixed bracket 212 having a complementary projection extending in opposition to the projection in member 214. The tubing 28 between receiver container 24 and blood processing bag 16 of FIG. 1 is passed between the two projections.

In operation the clamp 50 functions as follows. Initially the member 214 is in the position shown, and the flow of blood components through tube 28 is prevented by the force of spring 210 which pushes the projection on member 214 against the projection on bracket 212 thus clamping tubing 28 therebetween. As the rotor rotates causing blood components to centrifugally separate in bag 16; displacer fluid is generating pressure on the blood processing bag 16 tending to express the inner plasma-rich component from bag 16. Clamp 50 prevents this expulsion until the speed of the centrifuge rotor has reached a high enough value so that the centrifugal force as applied to the adjustment mass 206 is sufficient to overcome the opposing force from spring 210. When this occurs, the member 214 rotates in the direction of arrow 216 about pivot axle 204 compressing spring 210 and removing the projection on member 214 from compressive contact against tubing 28 thus opening the plasma line 28 to receiver bag 24.

Figure 3:
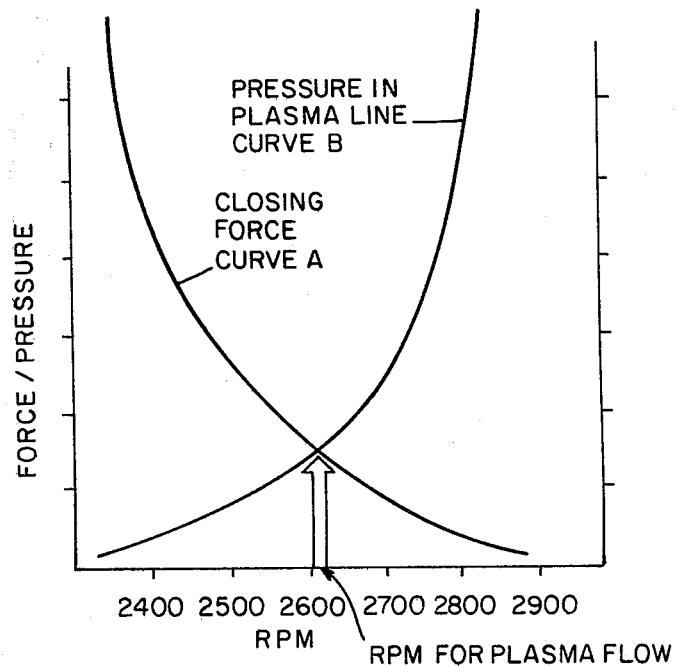
FIG. 3 is a graph showing the relationship between pressure in the plasma line and the closing force of the centrifugal switch as a function of rotor speed in revolutions per minute.

The closing force exerted on the tubing 28 from the centrifugal switch varies as the inverse of the square of the rotor rotational speed as shown by Curve A of FIG. 3. The pressure in the plasma line 28 varies as the square of the rotor rotational speed as shown by Curve B of FIG. 3. Accordingly, as graphically illustrated in FIG. 3 there exists, at the intersection of the two curves A and B, a very well defined and discrete rotational speed above which plasma will flow and below which plasma will not flow through tubing 28. In the example shown in FIG. 3, this critical speed is reached at 2600 revolutions per minute (r.p.m.).

It is therefore contemplated that the flow of plasma may be controlled in accordance with the invention by a two speed drive system; one of which speeds is below the critical speed, for example 2500 r.p.m. and the other of which is above the critical speed of the centrifugal switch, for example 2800 r.p.m. The centrifuge would be rotated at 2500 r.p.m. for a duration sufficient to separate plasma from whole blood and then switched to the higher r.p.m. to obtain plasma flow for a second duration. The plasma flow can then be stopped by switching back to the lower r.p.m.

Another more automatic method and apparatus for controlling the amount of plasma yield is shown in connection with FIGS. 4 and 5. In this embodiment, the reservoir 32 of FIG. 1 is replaced by a reservoir 132 shown in perspective in FIG. 4. Reservoir 132 consists of a generally cylindrical frame 136 having a cover 140 disposed at one end. At the center of the cover, an access vent 138 is located which serves the same purpose as the vent 38 in FIG. 1. A dial 150 connected to shaft 152 is rotatably mounted on the cover coaxial to vent 138.

An arcuate shaped disk 162 having a spiral groove 170 on its periphery is attached to the lower end of shaft 152. Immediately adjacent to disk 162 a tube guide 155 is fixedly attached to the frame of reservoir 132. Tube guide 155, as more clearly shown in FIG. 5, is provided with a guide slot 172. Disk 162 and guide 155 are disposed in relation to each other such that the slot 172 in the guide 155 and the groove 170 in the disk 162 are not aligned; rather slot 172 is disposed along the radius of the reservoir cylinder whereas groove 170 spirals inwardly towards the center of the cylinder.

The tubing 134 connecting the displacer bag 18 (of FIG. 1) to the reservoir to displacer fluid in reservoir 132 is passed through the groove 170 in disk 162 and also the slot 172 in guide 155.

Thus, when the dial 150 is rotated, for example, in the direction of the arrow 171, disk 162 is likewise rotated in the same direction and groove 170 tends to rotate tubing 134 in the same direction. However, slot 172 in guide 155 prevents the tubing from rotating and converts the tubing motion to a radially inward direction along slot 172.

When the centrifuge is rotating, the displacer fluid is forced against the cylindrical wall or frame 136 of the reservoir. Thus, moving the tubing 134 inwardly has the effect of decreasing the volume of displacer fluid which can leave the reservoir chamber and consequently decreasing the volume of plasma which is expressed from blood bag 16.

Dial 150 may be calibrated in accordance with the donor's hematrocrit to produce the desired plasma yield volume. For example, assume that the donor has a hematocrit of 40% in which case the donor's plasma yield would be about 270 ml. per 450 ml. of whole blood. The 40% hematocrit setting on dial 150 is therefore calibrated so that at this setting the tubing 134 is located along the radius of reservoir 132 so as to siphon off a sufficient volume of displacer fluid from the reservoir as will displace 270 ml. of plasma from the blood processing bag 16 of FIG. 1. Note that in this system, in order to maintain calibration the blood processing bag must be initially completely filled each time.

An alternative method would be to use a transparent cover 140 which is provided with a radial scale indicating the volume of displacer fluid in the reservoir. Knowing the donor's hematocrit and the amount of displacer fluid required to express a plasma yield in accordance with the donor's hematocrit; the centrifuge operator may simply observe the volume of displacer fluid being centrifugally pumped into displacer bag 18 from the reservoir as the rotor spins and turn the centrifuge off when the desired amount is attained.

Those skilled in the art will recognize many equivalents to the specific embodiments described herein. Such equivalents are considered part of this invention and are intended to be covered by the following claims.

I claim:

1. Apparatus for processing fluids, comprising, in combination:
   a. a centrifuge having a rotor capable of rotating about an axis of rotation at speeds sufficient to produce a desired separation;
   b. a processing chamber mounted on said rotor and supporting a flexible processing container and a flexible displacer fluid container;
   c. a reservoir of displacer fluid mounted on said rotor nearer the axis of rotation of the rotor than said processing chamber and in fluid communication with said displacer fluid container; whereby, when said rotor is rotated at a speed sufficiently long to produce the desired separation, displacer fluid flows due to centrifugal force from said reservoir to said displacer container thereby expanding said displacer container to expel a separate fluid component from said processing chamber; and
   d. a rotatable member provided to control the amount of displacer fluid communicated from said reservoir to said displacer fluid container thereby controlling the amount of fluid component expressed from said processing chamber.

2. A displacer fluid reservoir for supplying displacer fluid to a flexible displacer fluid container comprising:
   a hollow body for containing a reservoir of displacer fluid;
   an opening at one end of said hollow body adapted to be connected to a fluid communicating means;
   dial means rotatably mounted on said hollow body; and
   control means coupled to said dial for moving said fluid communicating means with respect to said displacer fluid in accordance with the position of the dial thereby to control the amount of displacer fluid removed from said reservoir when the reservoir is rotated.

3. The apparatus of claim 2 in which the control means comprises an arcuate disk having a spiral groove through which the fluid communicating means is passed and a guide member disposed adjacent said disk and having a longitudinal slot therein through which said fluid communicating means is also passed.

* * * * *